(12) United States Patent
Karvinen et al.

(10) Patent No.: US 8,597,903 B2
(45) Date of Patent: Dec. 3, 2013

(54) BIOTINIDASE ASSAY

(75) Inventors: Jarkko Karvinen, Turku (FI); Pertti Hurskainen, Piispanristi (FI); Pekka Mattsson, Turku (FI); Outi Mulari, Sauvo (FI); Jari Peuralahti, Turku (FI); Lassi Jaakkola, Littoinen (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 13/256,819

(22) PCT Filed: Mar. 10, 2010

(86) PCT No.: PCT/FI2010/050180
§ 371 (c)(1),
(2), (4) Date: Nov. 3, 2011

(87) PCT Pub. No.: WO2010/106222
PCT Pub. Date: Sep. 23, 2010

(65) Prior Publication Data
US 2012/0045784 A1    Feb. 23, 2012

(30) Foreign Application Priority Data
Mar. 16, 2009  (FI) .................................. 20090100

(51) Int. Cl.
*C12Q 1/34*  (2006.01)
*C07D 403/02*  (2006.01)
*C07D 235/00*  (2006.01)
*C07F 15/00*  (2006.01)

(52) U.S. Cl.
USPC ....... 435/18; 435/288.3; 435/287.9; 548/101; 548/255; 548/304.1

(58) Field of Classification Search
USPC ............. 435/18, 288.3, 287.9; 548/255, 101, 548/304.1; 544/215; 546/273.7
See application file for complete search history.

(56) References Cited

U.S. PATENT DOCUMENTS

| 5,630,996 A | 5/1997 | Reno et al. |
|---|---|---|
| 5,639,615 A | 6/1997 | Selvin et al. |

| 2006/0257963 A1 | 11/2006 | Cerda |
|---|---|---|
| 2007/0166810 A1 | 7/2007 | Bobrow et al. |
| 2012/0045784 A1* | 2/2012 | Karvinen et al. ............ 435/18 |

FOREIGN PATENT DOCUMENTS

WO        00/02051 A1    1/2000

OTHER PUBLICATIONS

Wastell, H., et al. "A Sensitive Fluorimetric Rate Assay for Biotinidase Using a New Derivative of Biotin, Biotinyl-6-aminoquinoline," Analytical Biochemistry, Jul. 1, 1984, pp. 69-73, vol. 140, No. 1.
Kobza, K., et al., "Biotinyl-methyl 4-(amidomethyl)benzoate is a competitive inhibitor of human biotinidase," Journal of Nutritional Biochemistry, Dec. 1, 2008, pp. 826-832, vol. 19, No. 12.
Hayakawa, Kou, et al., "Determination of Biotindase Activity with Biotinyl-6-aminoquinoline as Substrate," Methods in Enzymology, Jan. 1, 1997, pp. 435-442.
Livaniou, Evangelia, et al., "Determination of Serum Biotindase Activity with Radioiodinated Biotinylamide Analogs," Methods in Enzymology, Jan. 1, 1997, pp. 442-451.
International Search Report for PCT/FI2010/050180 dated Sep. 15, 2010.
Finnish Search Report for FI 20090100 dated Oct. 12, 2009.

* cited by examiner

*Primary Examiner* — Chih-Min Kam
(74) *Attorney, Agent, or Firm* — Sughrue Mion, PLLC (57) ABSTRACT

The present technology discloses biotinidase assay, biotinidase substrates (I) and a kit wherein the biotinidase substrate includes a label molecule separated from the biotin carbamoyl group by a linker X longer than about 4 Å but shorter than about 27 Å.

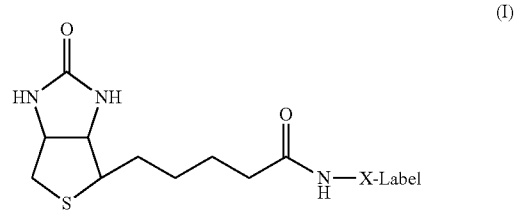

(I)

16 Claims, 3 Drawing Sheets

BIOTINIDASE ASSAY

CROSS REFERENCE TO RELATED APPLICATIONS

This application is a National Stage of International Application No. PCT/FI2010/050180, filed on Mar. 10, 2010, which claims priority from Finnish Patent Application No. 20090100, filed Mar. 16, 2009, the contents of all of which are incorporated herein by reference in their entirety.

FIELD

The technology described herein relates to an assay of measuring biotinidase level in samples.

BACKGROUND

Biotinidase deficiency is a disease caused by dysfunction of an enzyme called biotinidase. Patients having biotinidase deficiency experience severe clinical symptoms including irreversible neurological damage or even death. The gene defect for biotinidase deficiency is inherited and the disease typically emerges when two carriers pass it to their offspring. For each pregnancy of two such carriers, there is a 25% chance that the child will be born with the disease and a 50% chance the child will be a carrier for the gene defect. Studies show that approximately 1 of every 60,000 live births will have biotinidase deficiency. Infants with biotinidase deficiency appear normal at birth, but develop critical symptoms after the first weeks or months of life. With early diagnosis and treatment, all symptoms of this disease can be prevented.

In cells, biotinidase has the function of releasing biotin from biocytin and short biotinylated peptide chains for biotin recycling. Currently there are several available assays for measuring biotinidase activity in blood samples, although these assays are not always suited for clinical testing.

A method for measuring biotinidase activity using biotin coupled to fluorescent europium chelate has been disclosed (*Curr. Trends Infant Screening* 1989, 265). The cleavage of the amide bond between biotin and europium chelate resulted in a decrease in fluorescence intensity. Although the method might be suitable for quantitative homogenous measurement of biotinidase activity from serum, the method disclosed suffers from relatively high background signal and long incubation times.

SUMMARY

In this technology described herein, it was observed that when the biotinidase substrate is a biotin derivative wherein the carbamoyl group of the biotin moiety and the label are separated from each other by a linker length of which is longer than about 4 Å but shorter than about 27 Å, biotinidase assays can be developed.

According to one aspect this technology concerns a method of assaying biotinidase activity in a sample comprising: contacting said sample with a biotinidase substrate of the formula (I)

(I)

wherein X is a linker and wherein length the linker is from about 4 Å to about 27 Å.

In another aspect this technology concerns a biotinidase substrate of Formula (I)

(I)

wherein X is a linker comprising three to 15 moieties each moiety being independently selected from the group consisting of phenylene, alkylene containing 1-15 carbon atoms, ethynyldiyl (—C≡C—), ethylenediyl (—C═C—), ether (—O—), thioether (—S—), amide (—CO—NH—, —CO—NR'—, —NH—CO— and —NR'—CO—), carbonyl (—CO—), thiocarbonyl (C═S), ester (—COO— and —OOC—), carboxyl (—COOH and —COO⁻), carboxamido (—CONH$_2$), disulfide (—SS—), sulfone (—SO$_2$—), diaza (—N═N—), secondary amine and tertiary amine, wherein R' represents an alkyl group containing less than 5 carbon atoms, 2-hydroxy-1,3,5-triazinyl, 6-hydroxy-1,3,5-triazinyl, and 1H-1,2,3-triazol-4-yl to the proviso that the length of the linker is from about 4 Å to about 27 Å, and wherein the label is a luminescent or non-luminescent lanthanide(III) chelate.

In another aspect this technology concerns a kit for determination of biotinidase activity including: a microtiter plate and a biotinidase substrate according biotinidase substrate of Formula (I)

(I)

wherein X is a linker including three to 15 moieties each moiety being independently selected from the group consisting of phenylene, alkylene containing 1-15 carbon atoms, ethynyldiyl (—C≡C—), ethylenediyl (—C═C—), ether (—O—), thioether (—S—), amide (—CO—NH—, —CO—NR'—, —NH—CO— and —NR'—CO—), carbonyl (—CO—), thiocarbonyl (C═S), ester (—COO— and —OOC—), carboxyl (—COOH and —COO⁻), carboxamido (—CONH$_2$), disulfide (—SS—), sulfone (—SO$_2$—), diaza (—N═N—), secondary amine and tertiary amine, wherein R' represents an alkyl group containing less than 5 carbon atoms, 2-hydroxy-1,3,5-triazinyl, 6-hydroxy-1,3,5-triazinyl, and 1H-1,2,3-triazol-4-yl to the proviso that the length of the linker is from about 4 Å to about 27 Å; and wherein the label is a luminescent or non-luminescent lanthanide(III) chelate, and wherein the lanthanide is selected from europium, terbium, samarium and dysprosium.

DETAILED DESCRIPTION OF THE INVENTION

As defined herein the term "label" refers to any atom or molecule which can be used to provide a detectable (preferably quantitative) signal, and which can be attached covalently to biotin or derivatives thereof either directly or via a linker. Label may provide signal detectable by fluorescence, radioactivity, colorimetry, X-ray diffraction or absorption, enzymatic activity, and the like.

As defined herein, the term "non-luminescent lanthanide (III) chelate" is a lanthanide(III) chelate which does not include an aromatic structure which would absorb the excitation energy.

As defined herein, the term "luminescent lanthanide(III) chelate" is a lanthanide(III) chelate including an aromatic structure, which absorbs the excitation energy and transfers it to the lanthanide(III) ion.

As defined herein "organic chromophore" is a fluorescent or non-fluorescent label molecule including an aromatic subunit capable of absorbing light.

As defined herein, "quencher" molecule refers to a fluorescent or non-fluorescent molecule capable of accepting energy from the donor molecule.

As defined herein, "acceptor" molecule refers to a fluorescent molecule capable of accepting energy from the donor molecule.

As defined herein the term "linker" is a spacer between the biotin valeric carbamoyl group and the label molecule. The length of the linker can be estimated by using bond lengths of elements. Typical bond lengths are disclosed in Table 1.

TABLE 1

| Average Bond Lengths[a] | |
|---|---|
| Bond Type | Length; Å |
| C—C, parafinic | 1.541 |
| C—C, partial double bond | 1.53 |
| C—C, shortening in the presence of carbon oxygen double bond | 1.516 |
| C—C, shortening in the presence of two carbon oxygen double bond | 1.49 |
| C—C, shortening in the presence of one carbon-carbon triple bond | 1.46 |
| C—C in aromatic compounds | 1.395 |
| C=C | 1.337 |
| C=C, partial triple bond | 1.309 |
| C≡C | 1.205 |
| C—N, parafinic | 1.479 |
| C—N, aromatic | 1.426 |
| C—N, shortened, partial double bond | 1.322-1.352 |
| C—O, parafinic | 1.43 |
| C—O, shortened, partial double bond | 1.36 |
| C—S, parafinic | 1.81 |

TABLE 1-continued

| Average Bond Lengths[a] | |
|---|---|
| Bond Type | Length; Å |
| C—S, shortened, partial double bond | 1.73 |
| S—S | 1.89 |

[a]data from CRC Handbook of Chemistry and Physics, 50th edition

According to one embodiment the present disclosure concerns a method of assaying biotinidase activity in a sample containing biotinidase enzyme including: contacting of the sample with a biotinidase substrate of the formula (I)

wherein X is a linker. According to this disclosure the length of the linker is from about 4 Å to about 27 Å. In one embodiment, the length of the linker is from about 6 Å to about 23 Å. In an particular embodiment the length of the linker is from about 9 Å to about 15 Å. Exemplary length of the linker is about 12 Å and about 14 Å.

According to a particular embodiment the label selected from an organic chromophore, a luminescent lanthanide(III) chelate and a non-luminescent lanthanide(III) chelate. Exemplary organic chromophores are Alexa, QSY and BODIPY dyes available from Invitrogen (www.invitrogen.com), cyanine dyes from GE Healthcare (www.gelifesciences.com), dabcyl, dancyl, fluorescein, rhodamine, tetramethylrhodamine, TAMRA; HiLyte Fluors from AnaSpec (www.anaspec.com), DyLight dyes from Serotec (www.serotec.), BHQ dyes from Biosearch Technologies (www.biosearch.com), Oyster dyes from Denovo Biolabels (www.denovo.com) and Atto dyes from Atto-tec (www.atto-tec.de).

According to another embodiment, the lanthanide(III) chelate is non-luminescent. Exemplary non-luminescent chelates include a ligand selected from DTPA, EDTA, pyridine-2,6-diyl bis(methylenenitrilo)tetrakis(acetic acid) and diethylenetriamine-tetraacetic acid, and a lanthanide(III) ion selected from europium, terbium, dysprosium and samarium. In assays performed in whole blood the preferred non-luminescent lanthanide(III) chelate is based on DTPA. An exemplary DTPA based chelate is 1-(4-aminobenzyl)diethylenetriamine-N,N,N',N'',N''-pentaacetic acid lanthanide(III). This chelate can be linked to biotin or derivatives thereof via its amino group.

According to another embodiment, the lanthanide(III) chelate is luminescent. Exemplary luminescent lanthanide(III) chelates useful in the present technology are those disclosed in prior art categorized as a) pyridine analogues and their multimeric forms (U.S. Pat. No. 4,920,195, U.S. Pat. No. 4,801,722, U.S. Pat. No. 4,761,481, U.S. Pat. No. 4,459,186, EP 0770610, U.S. Pat. No. 5,216,134, U.S. Pat. No. 4,859, 777, U.S. Pat. No. 5,202,423, U.S. Pat. No. 5,324,825, U.S. patent application Ser. No. 11/004,061; U.S. patent application Ser. No. 10/928,143, PCT/FI2008/050494); b) DTPA conjugates with light-absorbing groups c) polymacrocyclic cage-type complexes such as cryptates (U.S. Pat. No. 4,927, 923, EP 493745 A), d) and others like calizarenes, podants, helicates and cyclic Schiff's bases (EP 0369000). According to a particular embodiment the luminescent lanthanide(III) chelate useful for the present technology includes an azacycloalkane backbone. An exemplary lanthanide(III) chelate including an azacycloalkane backbone is shown below.

According to one embodiment the linker X includes 3 to 15 moieties, each moiety being independently selected from the group consisting of phenylene, alkylene containing 1-15 carbon atoms, ethynyldiyl (—C≡C—), ethylenediyl (—C=C—), ether (—O—), thioether (—S—), amide (—CO—NH—, —CO—NR'—, —NH—CO— and —NR'—CO—), carbonyl (—CO—), thiocarbonyl (C=S), ester (—COO— and —OOC—), carboxyl (—COOH, and —COO⁻), carboxamido (—CONH$_2$), disulfide (—SS—), sulfone (—SO$_2$—), diaza (—N=N—), secondary amine and tertiary amine, wherein R' represents an alkyl group containing less than 5 carbon atoms, 2-hydroxy-1,3,5-triazinyl, 6-hydroxy-1,3,5-triazinyl and 1H-1,2,3-triazol-4-yl, to the proviso that the length of the linker is from about 4 Å to about 27 Å. In one embodiment, the length of the linker is from about 6 Å to about 23 Å. In an particular embodiment the length of the linker is from about 9 Å to about 15 Å. Exemplary length of the linker is about 12 Å and about 14 Å.

According to a particular embodiment the biotinidase substrates according to present technology includes a non-luminescent lanthanide(III) chelate, and is selected from a group consisting of Formulas (II) to (IV)

(II)

(III)

and

(IV)

wherein Ln is selected from europium, terbium, samarium and dysprosium. The length of the linker between the biotin carbamoyl group and the DTPA benzyl group is about 12 Å, 22 Å and 6 Å for substrates of Formula (II), (III) and (IV), respectively.

According to a particular embodiment the biotinidase substrate has the Formula (II)

The biotinidase substrates described herein can be used in variety of assay formats. According to one embodiment the signal detection is based on time resolved dissociative fluorescence enhancement. For sake of providing background, in dissociative fluorescence enhancement assays (DELFIA) polycarboxylate-based non-fluorescent lanthanide(III) chelates are used as labels. These chelates are applied as carriers (II)

wherein the lanthanide(III) ion is selected from europium, terbium, samarium and dysprosium. The preferable lanthanide ion is europium.

According to another embodiment the biotinidase substrate according to present technology includes a luminescent lanthanide(III) chelate. An exemplary biotinidase substrate including a luminescent lanthanide(III) chelate as the label has the Formula (V), wherein the length of the linker between the biotin carbamoyl group and the furyl group of the label is about 14 Å.

of the lanthanide(III) ions through the assay. After performing the assay, fluorescence is developed by dissociation of chelated ions and creating new fluorescent chelates in solution. This is achieved by decreasing conditional stability of the complexones by reduction of pH. Fluorinated β-diketones present in excess are able to form lanthanide complexes rapidly at the pH used. One lanthanide binds three diketones to form the light-harvesting group in the chelate. The remaining water molecules are removed with a synergistic agent, such as (V)

TOPO, and the newly formed complex is solubilized with detergents. Finally, lanthanide(III) content is measured fluorometrically.

In a particular embodiment a biotinidase substrate according to formula (I) including a luminescent or non-luminescent lanthanide(III) chelate as the label is incubated with other components in a sample well. The sample well is coated with a streptavidin binding material, such as an anti-streptavidin antibody. After incubation streptavidin (SA) is added to the reaction. Streptavidin binds to the anti-SA antibody and to the biotin moiety of the biotinidase substrate. The binding of the streptavidin to the biotinidase substrate stops the enzyme reaction. After incubation the sample well is washed with wash solution. Enhancement solution is added and after incubation lanthanide signal of the unreacted biotinidase substrate is measured. The enzyme activity is inversely proportional to the amount of the unreacted biotinidase substrate in the sample and thus leads to descending signal. When the label is a luminescent lanthanide(III) chelate the addition of enhancement solution can be omitted.

The methods for assaying biotinidase activity described herein are applicable to any sample containing or suspected of containing a biotinidase enzyme. The sample can thus be a biological sample, which can be obtained from an animal, cell culture, organism and fluids and cells thereof. Blood samples are commonly tested for biotinidase activity for detection of metabolic disorders in newborn babies. Any type of blood sample, including whole blood, blood fractions and currently popular blood-spot preparations can be used in the methods described herein.

According to another embodiment the substrate according to present technology includes a luminescent lanthanide(III) chelate, and the signal detection is based on time-resolved fluorescence energy transfer (TR-FRET) or time-resolved fluorescence energy quenching (TR-FQ). For sake of providing background, in assay based on TR-FRET, non-radiative energy-transfer takes place from the excited molecule, called the donor (here luminescent lanthanide(III) chelate), to another molecule, called the acceptor (organic chromophore). If the acceptor is fluorescent, the enzyme activity can be followed either by the disappearance of the acceptor signal or increase of the donor signal. If the acceptor is a non-fluorescent quencher capable of accepting energy from the donor, the biotinidase activity is followed as appearance of the donor signal upon cleavage. Exemplary donor molecules are the organic chromophores selected from alexa dyes, cyanine dyes, dabcyl, dancyl, fluorescein, rhodamine, TAMRA, bodiby, HiLyte Fluor647, DyLight649, QSY 7, tetramethylrodamine, BHQ dyes, and Oyster 650.

According to one embodiment the biotinidase substrate is labeled with a fluorophore and SA is labeled with a quencher, which quenches the fluorescence when the biotinidase substrate is intact. When biotinidase enzyme cleaves the biotin off from the substrate, fluorescence signal can be detected. The enzyme activity leads to increasing signal which is directly proportional to the biotinidase activity in the sample.

According to one embodiment the biotinidase substrate is labeled with a quencher, and SA is labeled with a fluorophore. The enzyme activity is directly proportional to increase of fluorescence signal. When biotinidase substrate is labeled with an acceptor, and SA with a donor, the enzyme activity is directly proportional to decrease of acceptor signal.

According to one embodiment the biotinidase substrate is labeled with a donor, and SA with an acceptor. The enzyme activity is directly proportional to increase or decrease of donor or acceptor signal dependent on the measurement.

The possible interference from blood components can be reduced by using a suitable correction algorithm or by diluting the sample.

According to a particular embodiment the present technology includes a method of assaying biotinidase activity in a blood sample containing biotinidase enzyme including:
a. placing the following contents in an anti-streptavidin coated sample well:
 (i) blood sample containing biotinidase enzyme
 (ii) biotinidase substrate according present technology wherein the label is luminescent or non-luminescent lanthanide(III) chelate,
b. incubating the contents of the sample well for sufficient time at sufficient temperature,
c. adding streptavidin to the sample well and incubating said contents of well for sufficient time at sufficient temperature,
d. washing the sample well with wash solution,
e. adding enhancement solution to the sample well and incubating the contents of well for sufficient time at sufficient temperature,
f. measuring the lanthanide signal, and
g. calculating the biotinidase activity based on lanthanide signal.

When the biotinidase substrate includes a luminescent lanthanide(III) chelate as the label, step e. can be omitted.

According to a particular embodiment the present technology includes a method of assaying biotinidase activity in a blood sample containing biotinidase enzyme including:
a. placing the following contents in a sample well:
 (i) blood sample containing biotinidase enzyme
 (ii) biotinidase substrate according present technology wherein the label is luminescent or non-luminescent lanthanide(III) chelate,
b. incubating the contents of said sample well for sufficient time at sufficient temperature,
c. transferring all or part of the contents of the sample well into another sample well coated with streptavidin,
d. incubating the contents of the sample well for sufficient time at sufficient temperature,
e. washing the sample well with wash solution,
f. adding enhancement solution to the sample well and incubating the contents of well for sufficient time at sufficient temperature,
g. measuring the lanthanide signal, and
h. calculating the biotinidase activity based on lanthanide signal.

When the biotinidase substrate includes a luminescent lanthanide(III) chelate as the label, step f. can be omitted.

According to a particular embodiment the present technology concerns a method of assaying biotinidase activity in a sample containing biotinidase enzyme and the biotinidase substrate according to Formulas (II) to (V). In a particular embodiment the sample is blood.

According to another embodiment, the present technology includes a method of assaying biotinidase activity in a blood sample containing biotinidase enzyme including:
a. placing the following contents in a sample well:
 (i) blood sample containing biotinidase enzyme,
 (ii) biotinidase substrate according present technology wherein the label is a donor molecule selected from a luminescent lanthanide(III) chelate and an organic chromophore,
b. incubating the contents of the sample well for sufficient time at sufficient temperature,
c. adding streptavidin labeled with an acceptor molecule, preferably a quencher molecule,
d. incubating the contents of the sample well for sufficient time at sufficient temperature,
e. measuring the fluorescence signal, and
f. calculating the biotinidase activity based on fluorescence signal.

According to another embodiment, the present technology includes a method of assaying biotinidase activity in a blood sample containing biotinidase enzyme including:
a. placing the following contents in a sample well:
  (i) blood sample containing biotinidase enzyme,
  (ii) biotinidase substrate according present technology wherein the label is an acceptor molecule, such as a quencher molecule,
b. incubating the contents of the sample well for sufficient time at sufficient temperature,
c. adding streptavidin labeled with a donor molecule selected from a luminescent lanthanide(III) chelate and an organic chromophore,
d. incubating the contents of the sample well for sufficient time at sufficient temperature,
e. measuring the fluorescence signal, and
f. calculating the biotinidase activity based on fluorescence signal.

According to another embodiment the present technology concerns a biotinidase substrate of Formula (I)

(I)

wherein X is a linker including three to 15 moieties each moiety being independently selected from the group consisting of phenylene, alkylene containing 1-15 carbon atoms, ethynyldiyl (—C≡C—), ethylenediyl (—C═C—), ether (—O—), thioether (—S—), amide (—CO—NH—, —CO—NR'—, —NH—CO— and —NR'—CO—), carbonyl (—CO—), thiocarbonyl (C═S), ester (—COO— and —OOC—), carboxyl (—COOH and —COO$^-$), carboxamido (—CONH$_2$), disulfide (—SS—), sulfone (—SO$_2$—), diaza (—N═N—), secondary amine and tertiary amine, wherein R' represents an alkyl group containing less than 5 carbon atoms, 2-hydroxy-1,3,5-triazinyl, 6-hydroxy-1,3,5-triazinyl, and 1H-1,2,3-triazol-4-yl to the proviso that the length of the linker is from about 4 Å to about 27 Å; and wherein the label is a luminescent or non-luminescent lanthanide(III) chelate, and the lanthanide is selected from euroium, terbium, samarium, and dysprosium. In one embodiment the length of the linker is from about 6 Å to about 23 Å. In a particular embodiment the length of the linker is from about 9 Å to about 15 Å. Exemplary length of the linker is about 12 Å and about 14 Å. Exemplary biotinidase substrates are substrates of Formulas (II), (III) and (IV) wherein non-luminescent lanthanide (III) chelates are used as labels, and biotinidase substrate of Formula (V) wherein a luminescent lanthanide(III) chelate is used as the label.

(II)

(III)

and (IV)

(V)

According to another embodiment the present technology concerns a kit for determination of biotinidase activity including: a microtiter plate and a biotinidase substrate according biotinidase substrate of Formula (I)

(I)

wherein X is a linker including three to 15 moieties each moiety being independently selected from the group consisting of phenylene, alkylene containing 1-15 carbon atoms, ethynyldiyl (—C≡C—), ethylenediyl (—C═C—), ether (—O—), thioether (—S—), amide (—CO—NH—, —CO—NR'—, —NH—CO— and —NR'—CO—), carbonyl (—CO—), thiocarbonyl (C═S), ester (—COO— and —OOC—), carboxyl (—COOH and —COO$^-$), carboxamido (—CONH$_2$), disulfide (—SS—), sulfone (—SO$_2$—), diaza (—N═N—), secondary amine and tertiary amine, wherein R' represents an alkyl group containing less than 5 carbon atoms, 2-hydroxy-1,3,5-triazinyl, 6-hydroxy-1,3,5-triazinyl, and 1H-1,2,3-triazol-4-yl to the proviso that the length of the linker is from about 4 Å to about 27 Å; and wherein the label is a luminescent or non-luminescent lanthanide(III) chelate. The microtitration plate according to this technology is coated with material capable of binding biotin. The preferable binding matrices/components are SA coated to a microtitration well directly or through anti-SA. According to a preferable embodiment the kit further includes one or more of: an assay buffer, wash buffer, enhancement buffer, calibrators and controls.

EXAMPLES

Example 1

The Synthesis of Biotin Tethered to DTPA (3)

(+)-Biotin (5.0 mg, 20.4 µmol) was dissolved in dry DMF (500 µA). N-hydroxysuccinimide (2.9 mg, 24.4 µmol) and DCC (5.0 mg, 24.4 µmol) were added, and the mixture was stirred overnight at ambient temperature before being evaporated to dryness. The residue including 1 was suspended in mixture of pyridine/water/TEA (9/1.5/0.1; v/v/v; (800 µL) and the europium chelate of 1-(4-aminobenzyl)diethylenetri-amine-N,N,N',N'',N''-pentaacetic acid (2; 21.2 mg, 30.6 mmol) predissolved in water (400 µL) was added. The mixture was stirred overnight at ambient temperature before being concentrated to ca 150 µL. Acetone (4.0 mL) was added, and the precipitation formed was collected by centrifugation, washed with acetone (4 mL) and dried. The crude product was purified on HPLC using a Shimadzu LC 10 AT instrument equipped with a diode array detector, a fraction collector and a reversed phase column (LiChrocart 125-3 Purospher RP-18e 5 µm). Mobile phase: (Buffer A): 0.02 M triethylammonium acetate (pH 7.0); (Buffer B): A in 50% (v/v) acetonitrile. Gradient: from 0 to 1 min 95% A, from 1 to 31 min from 95% A to 100% B. Flow rate was 0.6 mL min.$^{-1}$ Compound 3: ESI-TOF-MS [M-H]$^-$: calcd. 873.16. found 873.12.

Example 2

The Synthesis of Biotin-X Tethered to DTPA (5)

-continued

5

The synthesis was performed as disclosed in Example 1 but using biotinamidocaproate N-hydroxysuccinimide ester (4; Biotin-X-NHS). Compound 5: ESI-TOF-MS $[M-2H-]^{2-}$: calc. 492.62. found 492.58.

Example 3

The Synthesis of Biotin-XX Tethered to DTPA (7)

6

7

The synthesis was performed as disclosed in Example 1 but using biotinamidohexanoyl-6-aminohexanoic acid N-hydroxysuccinimide ester (6; Biotin-XX-NHS). Compound 7: ESI-TOF-MS $[M-2H]^{2-}$: calc. 549.16. found 549.15.

Example 4

The Synthesis of Biocytin Tethered to a Luminescent Lanthanide(III) Chelate (10)

Biocytin (8, 5 mg, 13 μmol) and the isothiocyanate chelate 9 (23 mg, 33 μmol) synthesized as disclosed in U.S. Pat. No. 4,920,195, were dissolved in the mixture of pyridine, water and triethylamine (9:1.5:01, v/v/v; 250 μL) and the mixture was stirred overnight at rt. The product was isolated by precipitation with acetone and purified with HPLC. Compound 10: ESI-TOF MS found, 1047.13; calcd for $C_{40}H_{46}EuN_8O_{12}S^-$ 1047.18. The product was prone to Edman degradation on prolonged storage at ambient temperature.

Example 5

The Synthesis of Biocytinamidohexylamine Labeled at its Amino Group with a Luminescent Europium(III) Chelate (12)

Biocytin (85 mg, 0.013 mmol) and Fmoc-aminohexanoic acid-NHS (predissolved in 150 μL of dioxane) was dissolved in the mixture of 0.1M NaHCO$_3$ (200 μL) and DMSO. The mixture was stirred overnight at rt. Piperidine (50 μL) was added, and the mixture was stirred for an additional 1 h before being concentrated to give compound II. ESI-TOF MS found, 484.22; calcd for C$_{22}$H$_{38}$N$_5$O$_5$S$^-$ 484.26. Reaction of compound 11 (0.013 mmol) with compound 9 (0.04 mmol) as described in Example 4 yielded compound 12. ESI-TOF MS found, 1160.21; calcd for C$_{46}$H$_{57}$EuN$_9$O$_{13}$S$^-$ 1160.27.

Example 6

The Synthesis of Biotin Labeled with Luminescent Lanthanide(III) Chelate 15

(+)-Biotin (5.0 mg, 20.4 mmol) dissolved in dry DMF (500 µL). N-hydroxysuccinimide (2.8 mg, 24.4 µmol) and DCC (5.0 mg, 24.4 µmol) were added, and the mixture was stirred overnight before being evaporated to dryness. 2-{4,7-bis {[4-(4-carboxy-3,5-dimethylfuran-2-yl)]-6-carboxypyridin-2-ylmethyl}-1,4,7-triazacyclononan-1-ylmethyl}-4-[4-(6-aminohexyl)aminocarbonyl-3,5-dimethylfuran-2-yl] pyridine-2-carboxylic acid europium(III) (13; 24.4 mg, 20.4 µmol) was suspended in mixture of pyridine/water/TEA (9/1.5/0.1; v/v/v) (800 µL) followed by addition of water (400 µL). Compound 14 was added, and the mixture was stirred overnight at room temperature. Water (1.0 mL) was added and pH was adjusted to 4 with 2 M HCl. The precipitation formed was collected by centrifugation and washed with acetone (2 mL). Purification was performed by preparative HPLC. ESI-TOF-MS [M-2H]$^{2-}$: calcd. 710.20. found 710.19.

Example 7

Heterogenous Biotinidase Assay (DELFIA)

A heterogenous assay is based on the use of streptavidin-specific antibody, streptavidin and biotinidase substrates (compounds 3, 5 and 7). Accordingly, 200 µA of anti-streptavidin antibody (1 µg per well, Novus Biologicals cat. No. NB200-448) was pipetted to the wells of the microplate in coating buffer (50 mM TRIS pH 7.4+50 mM NaCl). The plate was incubated at RT for 3 h. After that the plate was washed 2 times with Delfia Wash solution. The blood spots (diameter 3.2 mm) were punched to the wells. 10 nM of biotinidase substrate was added to the wells in reaction buffer (50 mM MES pH 6, 0.05% BSA, 0.01% TWEEN, 50 mM NaCl). The plate was incubated with slow shaking at +37° C. for 2 hours. 100 µA 20 nM streptavidin in reaction buffer was added into the wells. The plate was incubated for 1 hour at RT with slow shaking. The plate was washed for 4 times with Delfia Wash solution. 200 µA of Delfia Inducer was added to the wells and incubated for 15 minutes at RT. The Eu signal was measured with a time-resolved fluorometer. The more there is biotinidase enzyme in the sample the lower the Eu signal is.

Example 8

Homogenous Assay Based on Quenching (TR-FQ)

Figure 1:
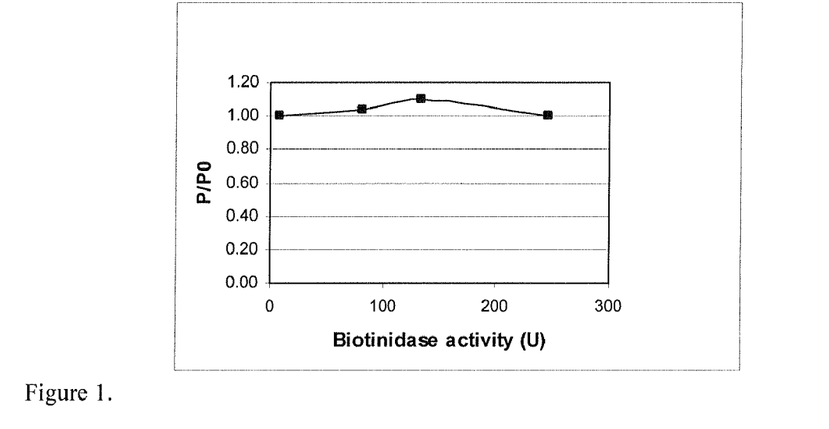
FIG. 1. Biotinidase assay using biotin derivative 3 as the substrate, wherein is no linker between the biotin valeroyl carbonyl group and the label. In a biotinidase assay compound 3 does not function as a substrate for the enzyme.
Figure 2:
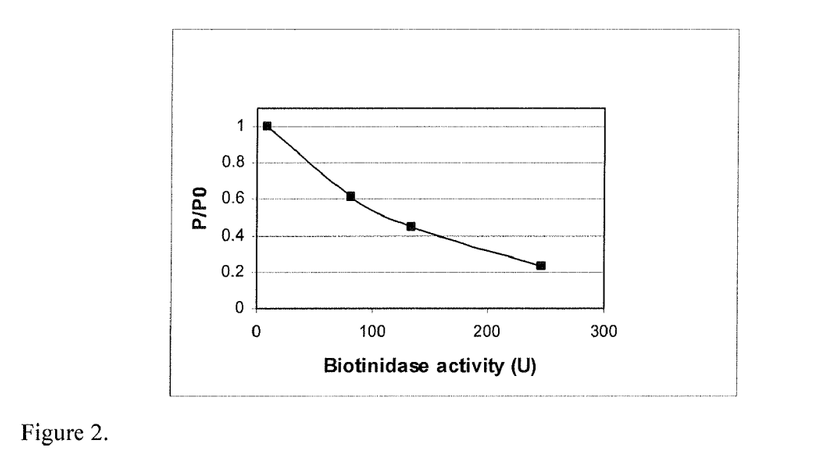
FIG. 2. Biotinidase assay using biotin derivative 5 as the substrate, wherein the length of the linker is ca 12 Å. In a biotinidase assay compound 5 functions as a favorable substrate for the enzyme.
Figure 3:
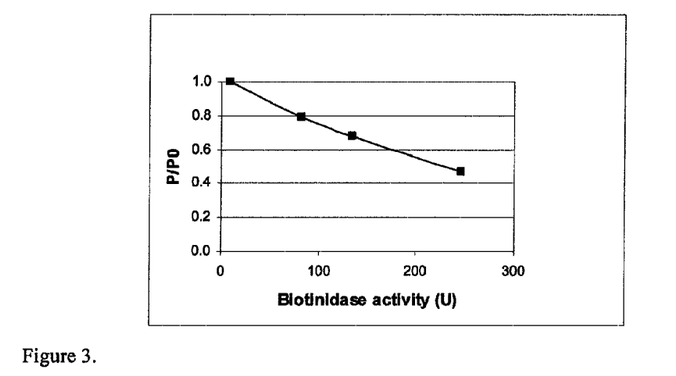
FIG. 3. Biotinidase assay using biotin derivative 7 as the substrate, wherein the length of the linker is ca 22 Å. In a biotinidase assay compound 7 functions moderately as a substrate for the enzyme.
Figure 4:
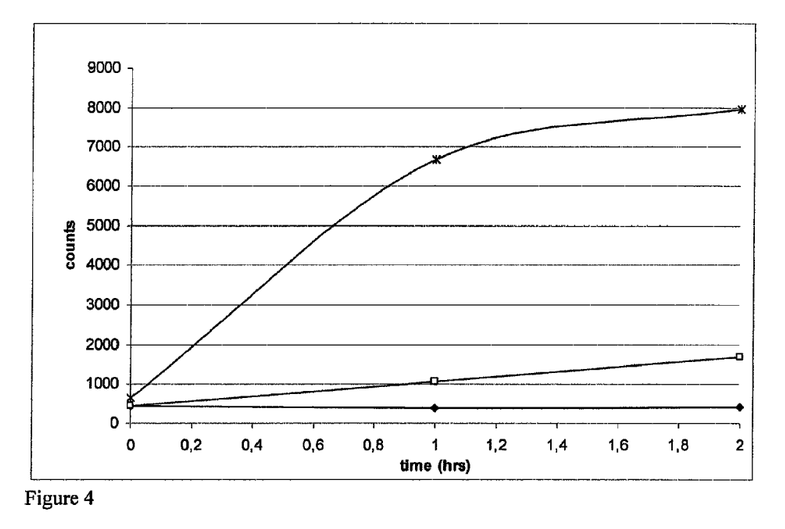
FIG. 4. Biotinidase assay using biotin derivative 10 as the substrate, wherein the length of the linker is ca 15 Å. Cross: normal human blood spot (high biotinidase activity); Square: lowest standard (porcine blood); diamond: abnormal human control (low biotinidase activity).
Figure 5:
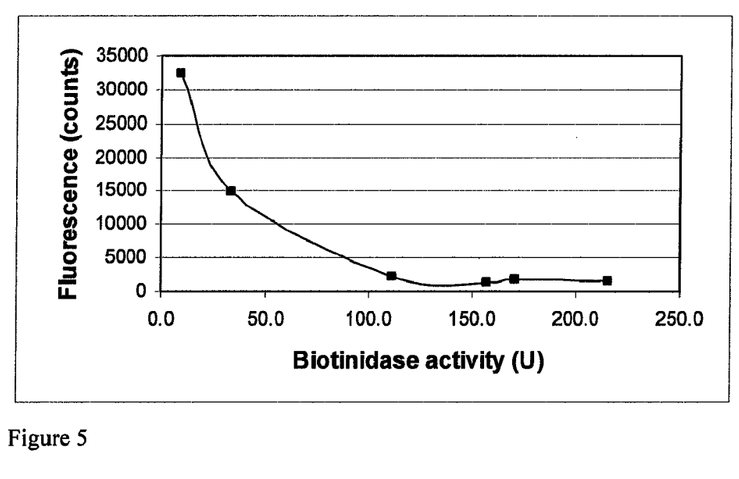
FIG. 5. Biotinidase assay using biotin derivative 15 (length of the linker ca 14 Å). The assay was performed in the absence of DELFIA inducer.
Figure 6:
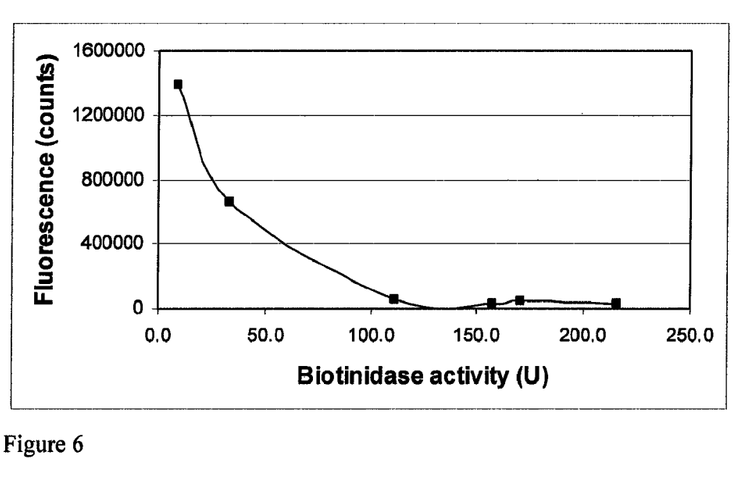
FIG. 6. Biotinidase assay using biotin derivative 15. The assay was performed in the presence of DELFIA inducer.

A homogenous assay for the detection of biotinidase activity is based on the europium labeled substrate and streptavidin labeled with a quencher. The blood spot (diameter 3.2 mm), calibrators and samples were punched to the wells of a microplate. The Eu-labeled biotinidase substrate (compound 10, 10 nM) was added in 100 µL of reaction buffer (50 mM TRIS pH 7, 0.2% BSA, 0.01% TWEEN, 50 mM NaCl. The plate was incubated at +37° C. for 3 h with slow shaking 10 nM of streptavidin labeled with a quencher molecule was added in 100 µL of reaction buffer. The plate was incubated at RT for 30 minutes with slow shaking protected from light. The Eu signal was measured on a time-resolved fluorometer. The more there is biotinidase enzyme in the sample the higher the Eu signal is. The results are shown in FIG. 4. Abnormal samples with low biotinidase activity can be easily identified from those with high biotinidase activity.

The following dyes were used as quenchers:

HiLyte Fluor 647 (AnaSpec, cat 81256)

DyLight 649 (Pierce, cat 46415)

Cy5 (Amersham GE Healthcare; PA25001)

Oyster 650 (Denovo biolabels; Oy-650-P-1-N-1)

Example 9

Heterogenous Assay Based on the Direct Measurement of Fluorescence of a Biotinidase Substrate Labeled with a Luminescent Lanthanide(III) Chelate The blood spot (diameter 3.2 mm), calibrators and samples were punched to the wells of a microplate. The Eu-labeled biotinidase substrate (compound 15, 10 nM) was added in 100 µL of reaction buffer (50 mM TRIS pH 7, 0.2% BSA, 0.01% TWEEN, 50 mM NaCl). The plate was incubated at +37° C. for 3 h with no shaking Streptavidin (10 nM/well) was added in 100 µL of reaction buffer. The plate was incubated at RT for 15 minutes with slow shaking followed by washing. The Eu signal was measured on a time-resolved fluorometer in the presence and absence of DELFIA Inducer (200 µL/well). It was observed that the assay performance was improved by addition of Inducer.

Example 10

Estimation of the Length of the Linker X

The estimation of the lengths of the linkers of the biotinidase substrates according to the present technology was performed as shown below for compound 5:

| Bond # | Length/Å |
| --- | --- |
| 1 | 1.479 |
| 2 | 1.541 |

-continued

| Bond # | Length/Å |
|---|---|
| 3 | 1.541 |
| 4 | 1.541 |
| 5 | 1.541 |
| 6 | 1.516 |
| 7 | 1.322 |
| 8 | 1.322 |
| sum | 11.80 |

The length of linker X is thus the sum of lengths of bonds 1-8, i.e. ca 12 Å.

The invention claimed is:

1. A method of assaying biotinidase activity in a sample comprising: contacting a sample with biotinidase substrate of the formula (I)

(I)

to assay the sample for biotinidase activity, measuring biotinidase activity using a label attached to the substrate, wherein X is a linker having a length from about 4 Å to about 27 Å and wherein the label is selected from the group of an organic chromophore, a luminescent lanthanide (III) chelate and a non-luminescent lanthanide (III) chelate.

2. The method according to claim 1 wherein the length said linker is from about 6 Å to about 23 Å.

3. The method according to claim 1 wherein the length said linker is from about 9 Å to about 15 Å.

4. The method according to claim 1, wherein the linker comprises three to 15 moieties each moiety being independently selected from the group consisting of phenylene, alkylene containing 1-15 carbon atoms, ethynyldiyl (—C≡C—), ethylenediyl (—C=C—), ether (—O—), thioether (—S—), amide (—CO—NH—, —CO—NR'—, —NH—CO— and —NR'—CO—), carbonyl (—CO—), thiocarbonyl (C=S), ester (—COO— and —OOC—), carboxyl (—COOH and —COO⁻), carboxamido (—CONH₂), disulfide (—SS—), sulfone (—SO₂—), diaza (—N=N—), secondary amine and tertiary amine, wherein R' represents an alkyl group containing less than 5 carbon atoms, 2-hydroxy-1,3,5-triazinyl, 6-hydroxy-1,3,5-triazinyl, and 1H-1,2,3-triazol-4-yl.

5. The method according to claim 1 wherein the label is a lanthanide(III) chelate.

6. The method according to claim 5, wherein the lanthanide (III) chelate comprises a ligand selected from diethylenetriaminepentaacetic acid (DTPA), ethylenediaminetetraacetic acid (EDTA), pyridine-2,6-diyl bis(methylenenitrilo)tetrakis (acetic acid) and diethylenetriaminetetraacetic acid and a lanthanide(III) ion selected from europium, terbium, dysprosium and samarium.

7. The method according to claim 5 wherein the lanthanide (III) chelate is luminescent.

8. The method according to claim 7 wherein the luminescent lanthanide(III) chelate comprises azacycloalkane backbone.

9. The method according to claim 5 wherein the lanthanide (III) chelate has the structure of and wherein one of the hydrogen atoms is replaced by the linker L.

10. The method according to claim 1 wherein the biotinidase substrate selected from the group consisting of wherein the lanthanide(III) ion is selected from europium, terbium, samarium and dysprosium.

11. The method according to claim 10 wherein the biotinidase substrate has the formula of 12. A biotinidase substrate of the formula (I)

(I)

wherein X is a linker comprising three to 15 moieties each moiety being independently selected from the group consisting of phenylene, alkylene containing 1-15 carbon atoms, ethynyldiyl (—C≡C—), ethylenediyl (—C=C—), ether (—O—), thioether (—S—), amide (—CO—NH—, —CO—NR'—, —NH—CO— and —NR'—CO—), carbonyl (—CO—), thiocarbonyl (C=S), ester (—COO— and —OOC—), carboxyl (—COOH and —COO⁻), carboxamido (—CONH₂), disulfide (—SS—), sulfone (—SO₂—), diaza (—N=N—), secondary amine and tertiary amine, wherein R' represents an alkyl group containing less than 5 carbon atoms, 2-hydroxy-1,3,5-triazinyl, 6-hydroxy-1,3,5-triazinyl, and 1H-1,2,3-triazol-4-yl to the proviso that the length of said linker is from about 6 Å to about 27 Å, and the label is a luminescent lanthanide(III) chelate or a non-luminescent lanthanide(III) chelate comprising a ligand selected from diethylenetriaminepentaacetic acid (DTPA), ethylenediaminetetraacetic acid (EDTA), pyridine-2,6-diyl bis(methylenenitrilo) tetrakis(acetic acid) and diethylenetriaminetetraacetic acid and, wherein said lanthanide is selected from europium, terbium, dysprosium and samarium.

13. A kit for determination of biotinidase activity comprising: a microtiter plate and a biotinidase substrate according to claim 12.

14. The kit according to claim 13 wherein said plate is coated with anti-streptavidin antibody.

15. The kit according to claim 13 wherein said plate is coated with streptavidin.

16. The kit according to claim 13 further comprising: one or more components selected from an assay buffer, wash buffer, enhancement buffer, calibrator and control sample.

\* \* \* \* \*